US005223408A

United States Patent [19]

Goeddel et al.

[11] Patent Number: 5,223,408

[45] Date of Patent: Jun. 29, 1993

[54] METHOD FOR MAKING VARIANT SECRETED PROTEINS WITH ALTERED PROPERTIES

[75] Inventors: David V. Goeddel, Hillsborough; Glenn C. Rice, Palo Alto; David W. H. Leung, Foster City, all of Calif.

[73] Assignee: Genentech, Inc., South San Francisco, Calif.

[21] Appl. No.: 728,456

[22] Filed: Jul. 11, 1991

[51] Int. Cl.[5] ...................... C12P 21/02; C12N 15/62; C12N 15/58; C12N 15/53

[52] U.S. Cl. ................................. 435/69.3; 435/69.4; 435/69.52; 435/69.6; 435/69.7; 435/172.3; 435/189; 435/195; 435/215; 435/216; 435/226

[58] Field of Search .................... 435/69.7, 70.1, 226, 435/320.1, 172.3, 69.3, 69.4, 69.52, 69.6, 189, 195, 215, 216

[56] References Cited

PUBLICATIONS

Johnston et al., *Proc. Natl. Acad. Sci. USA*, 80: 3711-3715 (1983).

Schroff et al., *J. Immunol. Methods*, 70: 167-177 (1984).

Rice et al., *Cytometry*, 12: 221-233 (1991).

Dangl et al. (1982), J. Immunol. Meth., vol. 52, pp. 1-14.

Botstein et al. (Sep. 20, 1985), Science, vol. 229, pp. 1193-1201.

Caras et al. (Nov. 27, 1987), Science, vol. 238, pp. 1280-1283.

Pennica et al. (Jan. 20, 1983), Nature, vol. 301, pp. 214-221.

*Primary Examiner*—Richard A. Schwartz
*Assistant Examiner*—Philip W. Carter
*Attorney, Agent, or Firm*—Daryl B. Winter

[57] ABSTRACT

A screening method for the selection of mutagenized proteins that are normally secreted by cells is described. The method includes the development of a cloning vector for the expression of secretory proteins as fusion proteins on the cell surface of transfected mammalian cells. The secreted protein is displayed on the cell surface by fusion with the glycophospholipid membrane anchor of decay accelerating factor (DAF). Tissue-type plasminogen activator (t-PA), which is normally secreted, is used as a model protein. PCR mutagenesis is used to generate random mutations within the Kringle 1 (K1) domain of t-PA. Fluorescence activated cell sorting (FACS) is employed to screen for t-PA mutants possessing a loss of an epitope to a specific Mab, whose nonlinear binding domains overlap with the t-PA clearance receptor contact regions novel t-PA mutants designated N115S, N1425S, and K159R were discovered by this method.

12 Claims, 4 Drawing Sheets

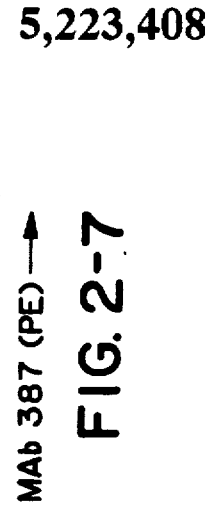
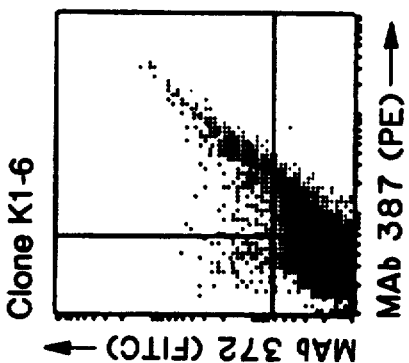
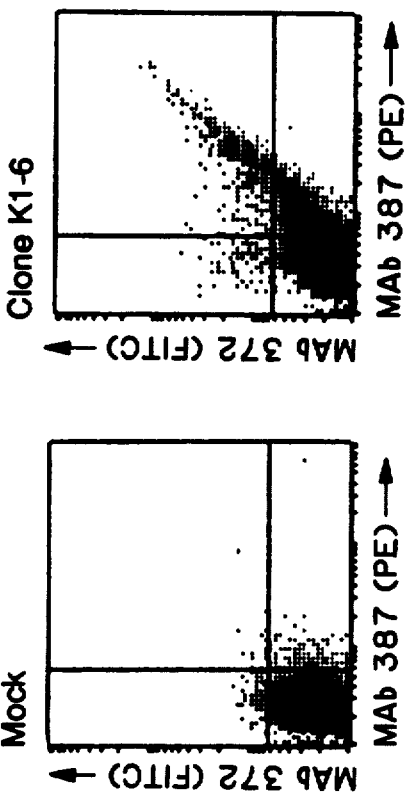
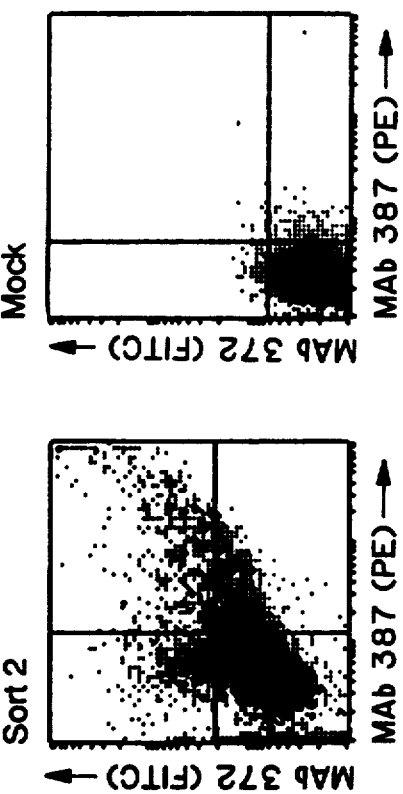
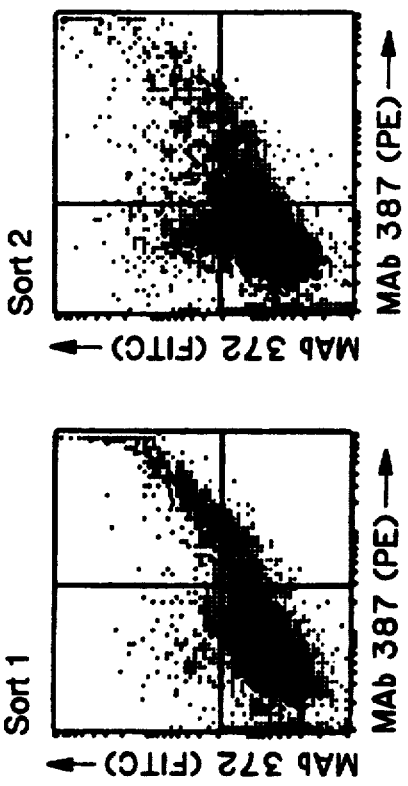
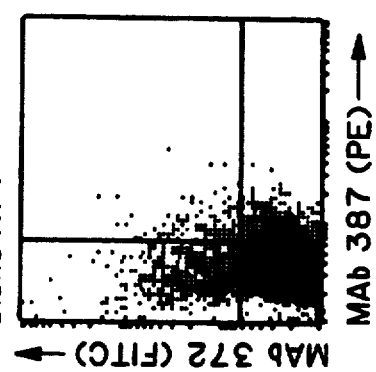
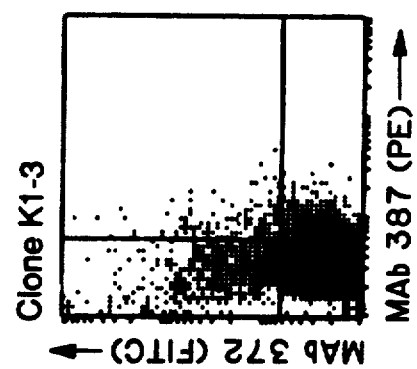
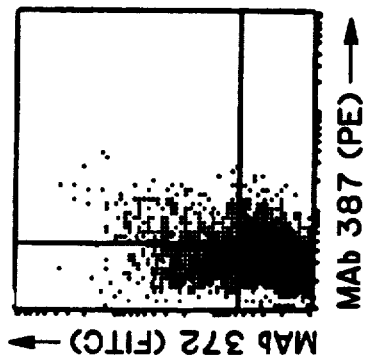

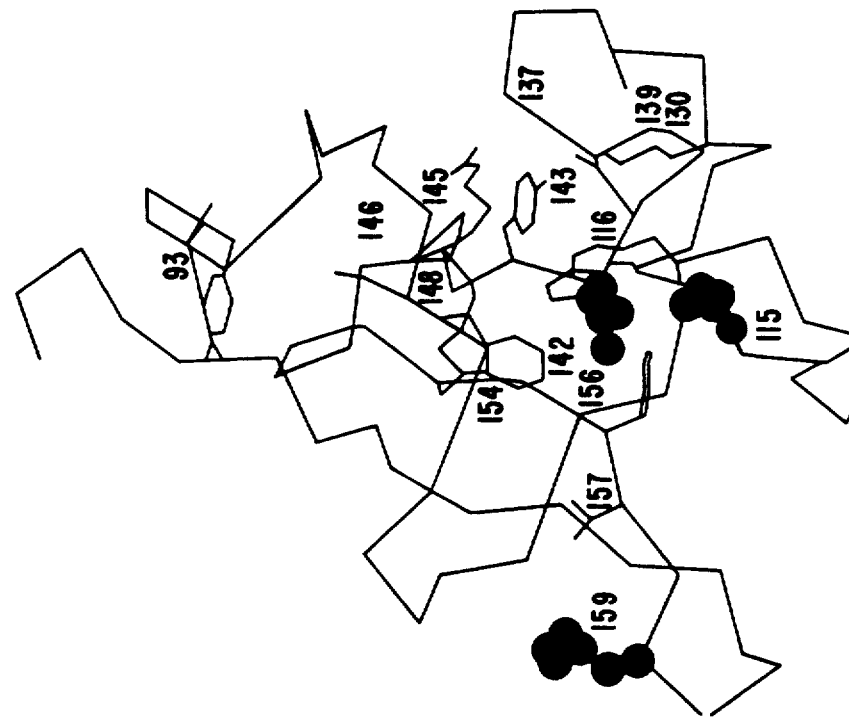
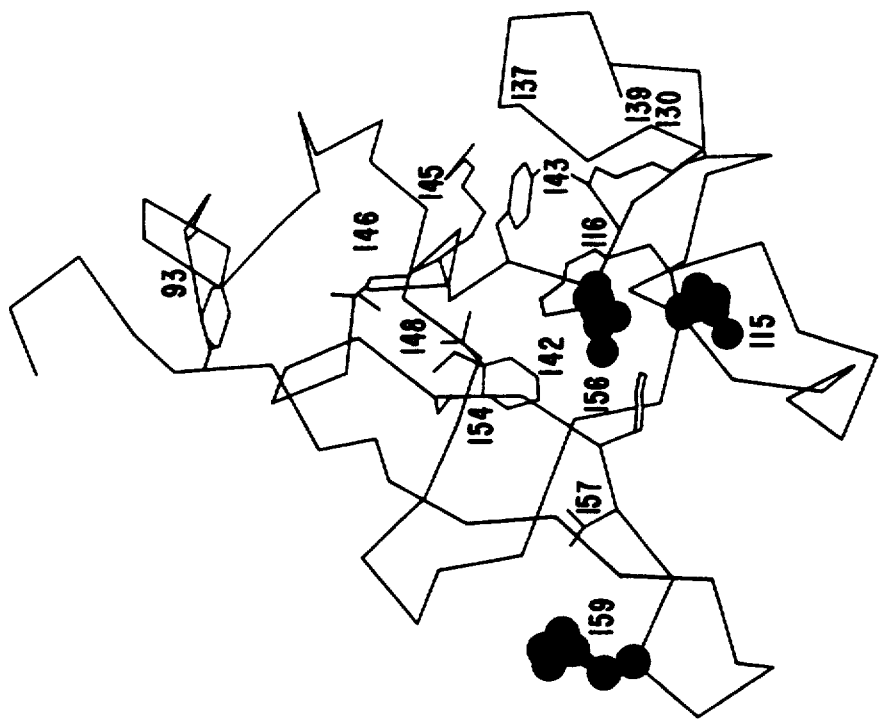
FIG. 3

METHOD FOR MAKING VARIANT SECRETED PROTEINS WITH ALTERED PROPERTIES

FIELD OF THE INVENTION

This invention relates to the preparation and systematic selection of novel binding proteins having altered properties. Specifically, this invention relates to methods for producing variant non-membrane proteins having altered binding properties when compared to the wild-type protein. In preferred embodiments, the invention is directed to the preparation of variant secreted proteins that retain at least one desired binding property and that have lost at least one undesired binding property relative to the wild-type protein. The invention further relates to novel tissue-type plasminogen activator mutants prepared by the method of the invention.

BACKGROUND OF THE INVENTION

I. Methods for making novel binding partners

Binding partners are substances that specifically bind to one another, usually through noncovalent interactions. Examples of binding partners include ligand-receptor, antibody-antigen, drug-target, and enzyme-substrate interactions. Binding partners are extremely useful in both therapeutic and diagnostic fields.

Binding partners have been produced in the past by a variety of methods including; harvesting them from nature (e.g., antibody-antigen, and ligand-receptor pairings) and by adventitious identification (e.g. traditional drug development employing random screening of candidate molecules). In some instances these two approaches have been combined. For example, variants of proteins or polypeptides, such as polypeptide fragments, have been made that contain key functional residues that participate in binding. These polypeptide fragments, in turn, have been derivatized by methods akin to traditional drug development. An example of such derivatization would include strategies such as cyclization to conformationally constrain a polypeptide fragment to produce a novel candidate binding partner.

The problem with prior art methods is that naturally occurring ligands may not have proper characteristics for all therapeutic applications. Furthermore, methods for making non-naturally occurring synthetic binding partners are often expensive and difficult, usually requiring complex synthetic methods to produce each candidate. The inability to characterize the structure of the resulting candidate so that rational drug design methods can be applied for further optimization of candidate molecules further hampers these methods.

In an attempt to overcome these problems, Geysen (Geysen, *Immun. Today*, 6:364–369 [1985]); and (Geysen et al., *Mol. Immun.*, 23:709–715 [1986]) has proposed the use of polypeptide synthesis to provide a framework for systematic iterative binding partner identification and preparation. According to Geysen et al., Ibid, short polypeptides, such as dipeptides, are first screened for the ability to bind to a target molecule. The most active dipeptides are then selected for an additional round of testing comprising linking, to the starting dipeptide, an additional residue (or by internally modifying the components of the original starting dipeptide) and then screening this set of candidates for the desired activity. This process is reiterated until the binding partner having the desired properties is identified.

The Geysen et al. method suffers from the disadvantage that the chemistry upon which it is based, peptide synthesis, produces molecules with ill-defined or variable secondary and tertiary structure. As rounds of iterative selection progress, random interactions accelerate among the various substituent groups of the polypeptide so that a true random population of interactive molecules having reproducible higher order structure becomes less and less attainable. For example, interactions between side chains of amino acids, which are sequentially widely separated but which are spatially neighbors, freely occur. Furthermore, sequences that do not facilitate conformationally stable secondary structures provide complex peptide-sidechain interactions which may prevent sidechain interactions of a given amino acid with the target molecule. Such complex interactions are facilitated by the flexibility of the polyamide backbone of the polypeptide candidates. Additionally, candidates may exist in numerous conformations making it difficult to identify the conformer that interacts or binds to the target with greatest affinity or specificity complicating rational drug design.

To overcome many of the problems inherent in the Geysen approach, biological selection and screening has been chosen as an alternative approach. Biological selections and screens are powerful tools to probe protein function and to isolate variant proteins with desirable properties (Shortle, *Protein Engineering*, Oxender and Fox, eds., A. R. Liss, Inc., New York, pp. 103–108 [1988]) and Bowie et al., *Science*, 247:1306–1310 [1990]). However, a given selection or screen is applicable to only one or a small number of related proteins.

Recently, Smith and coworkers (Smith, *Science*, 228: 1315–1317 [1985]) and Parmley and Smith, *Gene*, 73:305–318 [1985] have demonstrated that small protein fragments (10–50 amino acids) can be "displayed" efficiently on the surface of filamentous phage by inserting short gene fragments into gene III of the fd phage ("fusion phage"). The gene III minor coat protein (present in about 5 copies at one end of the virion) is important for proper phage assembly and for infection by attachment to the pili of *E. coli* (see Rasched et al., *Microbiol. Rev.*, 50: 401–427 [1986]). Recently, "fusion phage" have been shown to be useful for displaying short mutated peptide sequences for identifying peptides that may react with antibodies (Scott et al., *Science* 249: 386–390, [1990]) and Cwirla et al., *Proc. Natl. Acad. U.S.A.* 87:6378–6382, [1990]). or a foreign protein (Devlin et al., *Science*, 249: 404–406 [1990]).

Ladner (WO 90/02802) discloses a method for selecting novel binding proteins displayed on the outer surface of cells and viral particles where it is contemplated that the heterologus proteins may have up to 164 amino acid residues. The method contemplates isolating and amplifying the displayed proteins to engineer a new family of binding proteins having desired affinity for a target molecule. More specifically, Ladner describes a "fusion phage" displaying proteins having "initial protein binding domains" ranging from 46 residues (crambin) to 164 residues (T4 lysozyme) fused to the M13 gene III coat protein. Small fusion proteins, such as BPTI, are preferred when the target is a protein or macromolecule, while larger fusion proteins, such as T4 lysozyme, are preferred for small target molecules such as steroids because such large proteins have clefts and grooves into which small molecules can fit. The preferred protein, BPTI, is proposed to be fused to gene III at the site disclosed by Smith et al. or de la Cruz et al., *J. Biol. Chem.*, 263: 4318–4322 [1988], or to one of the terminii, along with a second synthetic copy of gene III so that "some" unaltered gene III protein will be present. Ladner does not address the problem of successfully panning high affinity peptides from the random peptide library which plagues the biological selection and screening methods of the prior art.

To overcome problems associated with the Ladner approach, Bass, S., et al., *Proteins* 8:309-314 (1990) have devised a method for displaying single copies of mutant fusion proteins, especially human growth hormone, on the surface of the filamentous phage M13. This expression system allows large proteins with discontinuous binding epitopes to be displayed on the surface of the filamentous phage and permits biological selections to be applied to mutant gene III fusions. These authors do not describe bivariant biological selection of fusion proteins displayed on mammalian cell surfaces.

II. Tissue-type Plasminogen Activator (t-PA) variants

A substantially pure form of t-PA was first produced from a natural source and tested for in vivo activity by Collen et al., U.S. Pat. No. 4,752,603 issued Jun. 21, 1988 (see also Rijken et al., *J. Biol. Chem.*, 256:7035 [1981]). Pennica et al. (*Nature*, 301:214 [1983]) determined the DNA sequence of t-PA and deduced the amino acid sequence from this DNA sequence (see U.S. Pat. No. 4,766,075 issued Aug. 23, 1988).

Research on the structure of t-PA has identified the molecule as having five domains. Each domain has been defined with reference to homologous structural or functional regions in other proteins such as trypsin, chymotrypsin, plasminogen, prothrombin, fibronectin, and epidermal growth factor (EGF). These domains have been designated, starting at the N-terminus of the amino acid sequence of t-PA, as the finger (F) domain from amino acids 1 to about 44, the growth factor (G) domain from about amino acids 45 to 91 (based on homology with EGF), the kringle-1 (K1) domain from about amino acids 92-173, the kringle-2 (K2) domain from about amino acids 180 to 261, and the serine protease (P) domain from about amino acid 264 to the carboxyl terminus at amino acid 527. These domains are situated essentially adjacent to each other, and some are connected by short "linker" regions. These linker regions bring the total number of amino acids in the mature polypeptide to 527.

Each domain is believed to confer certain biologically significant properties on the t-PA molecule. The finger domain is thought to be important in the high binding affinity of t-PA to fibrin. Structural determinants for plasma clearance are thought to be on the finger, growth factor, and kringle-1 domains. The kringle-2 domain is responsible for binding to lysine. The serine protease domain is responsible for the enzymatic activity of t-PA and the fibrin specificity.

t-PA variants with decreased clearance have been prepared by deleting individual amino acids, partial domains, or complete domains from the molecule. For example, removal of part or all of the finger domain of t-PA as described in U.S. Pat. No. 4,935,237 (issued Jun. 19, 1990) results in a molecule with decreased clearance, although it has substantially diminished fibrin-binding characteristics. Browne et al. (*J. Biol. Chem.*, 263:1599 [1988]) deleted the region between amino acids 57 and 81 and found the resulting variant to have a slower clearance from plasma. Collen et al. (*Blood*, 71:216 [1988]) deleted amino acids 6-86 (part of the finger and growth domains) and found that this mutant had a half-life in rabbits of 15 minutes as compared with 5 minutes for wild-type t-PA. Similarly, Kaylan et al. (*J. Biol. Chem.*, 263:3971 [1988]) deleted amino acids 1-89 and found that the half-life of this mutant in mice was about fifteen minutes as compared to about two minutes for wild-type t-PA. Cambier et al. (*J. Cardiovasc. Pharmacol.*, 11:468 [1988]) constructed a variant with the finger and growth factor domains deleted and the three asparagine glycosylation sites abolished. This variant was shown to have a longer half-life than wild-type t-PA when tested in dogs. Variants with only the growth factor domain or the finger domain deleted have also been demonstrated to have decreased clearance rates in rabbits, guinea pigs and rats (Higgins and Bennett, *Ann. Rev. Pharmacol. Toxicol.*, 30:91 [1990] and references therein).

A variety of amino acid substitution t-PA variants have been evaluated for their ability to decrease the clearance rate or increase the half-life of t-PA. The variant R275E (where arginine at position 275 of native, mature t-PA was substituted with glutamic acid) has been shown to have a clearance rate of about two times slower than that of wild-type t-PA when tested in primates and rabbits (Hotchkiss et al., *Thromb. Haemost.*, 58:491 [1987]). Substitutions in the region of amino acids 63-72 of mature, native t-PA, and especially at positions 67 and 68, have been reported to increase the plasma half-life of t-PA (see WO 89/12681, published Dec. 28, 1989).

Production of other substitution variants has focused on converting the glycosylation sites of t-PA to non-glycosylated sites. Hotchkiss et al. (*Thromb. Haemost.*, 60:255 [1988]) selectively removed oligosaccharide from the t-PA molecule, and demonstrated that the removal of these residues decreased the rate of clearance of t-PA when tested in rabbits. Removal of the high mannose oligosaccharide at position 117 using the enzyme endo--N-acetylglucosaminidase H (Endo-H) resulted in a rate of clearance that was decreased about two fold. Oxidation of nearly all oligosaccharide residues using sodium periodate resulted in a rate of clearance nearly three fold lower than wild-type t-PA. These researchers also generated the t-PA variant N117Q (wherein asparagine at position 117 of native, mature t-PA was substituted with glutamine) to prevent glycosylation at position 117. The clearance rate of this variant was lower than wild-type t-PA. See also EP 238,304 published Sep. 23, 1987 and EP 227,462 published Jul. 1, 1987.

An additional approach to produce t-PA variants with extended circulatory half-life and slower clearance has been to add glycosylation sites to the molecule. As examples of this approach, positions 60, 64, 65, 66, 67, 78, 79, 80, 81, 82, and 103 have been substituted with appropriate amino acids to create molecules with glycosylation sites at or near some of these residues (see WO 89/11531, published Nov. 30, 1989 and U.S. Ser. No. 07/480,691, filed Feb. 15, 1990).

A general review of plasminogen activators and second-generation derivatives thereof can be found in Harris, *Protein Engineering*, 1: 449-458 (1987). Other reviews of t-PA variants include Pannekoek et al., *Fibrinolysis*, 2: 123-132 (1988), Ross et al., in *Annual Reports in Medicinal Chemistry*, Vol. 23, Chapter 12 (1988), and Higgins and Bennett, supra.

Accordingly, it is an object of this invention to provide a rapid and effective method for the systematic preparation of candidate binding substances.

It is another object of this invention to prepare candidate binding substances that are displayed on the surface of mammalian cells and that are conformationally stable.

It is still another object of this invention to prepare candidate binding substances comprising fusion proteins of a transmembrane anchor polypeptide and a heterologous protein where the heterologous protein is non-membranous and soluble, especially a secretory protein, and displayed on a cell, especially mammalian, where the fusion protein is encoded by DNA contained in a plasmid and the plasmid is transfected into a host cell.

It is a further object of this invention to provide a method for the preparation and selection of desired variant binding proteins employing a bivariant selection process in which the proteins are expressed on a mammalian cell surface and in which the proteins retain at least one binding property in common with, and one binding property different from the corresponding wild-type protein.

It is a still further object of this invention to provide novel t-PA mutants or variants having diminished binding affinity for receptors responsible for t-PA clearance.

These and other objects of this invention will be apparent from consideration of the invention as a whole.

SUMMARY OF THE INVENTION

These objectives have been achieved by providing a method for making a variant protein having at least one binding property in common with, and at least one binding property different from, a selected wild-type protein. The method comprises (a) obtaining at least a first and second reporter molecule capable of binding to different epitopes on the selected wild-type protein; (b) mutating DNA encoding the selected wild-type protein thereby creating a library of related variant DNA molecules; (c) inserting each DNA molecule created in step (b) into an expression vector, wherein the vector comprises DNA encoding a transmembrane anchor domain thereby creating a library of vectors; (d) transfecting eukaryotic cells, preferably mammalian, with the vectors of step (c); (e) culturing the cells of step (d) under conditions inducing the expression of the DNA to produce a chimeric fusion protein immobilized on the cell membrane; (f) contacting the cultured cells of step (e) with the first and second reporter molecules under conditions for which at least a portion of the cultured cells bind to the first or second reporter molecules; (g) sorting the contacted cells, preferably by fluoresence activated cell sorting (FACS), based on a desired binding pattern with the first or second reporter molecules; and (h) obtaining the variant proteins having the desired binding pattern from the sorted cells from (g). The preferred binding pattern comprises binding the cells with the first reporter molecule and the absence of binding of the cells with the second reporter molecule.

The method alternatively comprises isolating the variant protein from the sorted cells or producing the variant protein by recombinant methods from the variant DNA molecule isolated from the sorted cells. Another alternative comprises sequencing the variant DNA molecule, determining the codons encoding amino acids in the variant protein that produce the desired binding pattern, altering those codons in a DNA molecule encoding the wild-type protein, and producing the variant protein from the DNA containing the altered codons by recombinant methods.

The first and second reporter molecules generally comprise a detectable marker conjugated to a molecule selected from; antibodies, ligands, and soluble receptors that are capable of binding with the wild-type protein. The first and second reporter molecules are typically monoclonal antibodies (Mabs) each conjugated to a different fluorophore. Normally the fluorophores will be fluorescein or phycoerythrin.

The transmembrane anchor domain will preferably be the membrane glycophospholipid anchor sequence of decay acceleration factor (DAF). Also preferably, the selected wild-type protein is selected from; growth hormone, human growth hormone (hGH), des-N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormone (FSH), thyroid stimulating hormone (TSH), leutinizing hormone (LH), glycoprotein hormone receptors, calcitonin, glucagon, factor VIII, an antibody, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, $\beta$-lactamase, tissue factor protein, inhibin, activin, vascular endothelial growth factor, integrin receptors, thrombopoietin, protein A or D, rheumatoid factors, NGF-$\beta$, platelet-growth factor, transforming growth factor; TGF-alpha and TGF-beta, insulin-like growth factor-I and -II, insulin-like growth factor binding proteins, CD-4, DNase, latency associated peptide, erythropoietin, osteoinductive factors, interferon, alpha, -beta, and -gamma, colony stimulating factors (CSFs), M-CSF, GM-CSF, and G-CSF, interleukins (ILs), IL-1, IL-2, IL-3, IL-4, IL-6, IL-7, superoxide dismutase; viral antigens, HIV envelope proteins GP120 and GP140, immuno globulins, and fragments of the above-listed proteins. The selected wild-type protein is more preferably a human protein, and most preferably a secreted protein.

The objects of the invention are further achieved by providing a t-PA amino acid sequence variant molecule comprising a substitution at one or more of the amino acid residues; 115, 142, and 159, where the substitutions at residues 115 and 142 may optionally be; charged residues, aliphatic residues, aromatic residues, or non-polar residues and where the substitutions at residue 159 may optionally be; acidic residues or uncharged residues. Preferred t-PA amino acid sequence substitutional variant molecules are: Y93C,T103A,N184S,G198D; N115S,G139R; N146I,G198D; S127C,Y143H,C173R; V157D; R130Q,K159R; R89G,W116R,K124E,D148-G,Y156F,Y163C,N177S,Y181C,F182L,N184T; G137D,W154R; N142S; and Y156D. More preferred t-PA amino acid sequence substitutional variant molecules are; N115S, N142S, and K159R.

The invention includes a DNA molecule encoding the variant t-PA molecules, a replicable expression vector capable, in a transformed host cell, of expressing the DNA sequence, and the transformed host cells themselves.

Finally, the invention includes a composition for treating a vascular condition or disease comprising a therapeutically effective amount of the above described t-PA variants in admixture with a pharmaceutically acceptable carrier. The composition is used in a method for treating a vascular condition or disease in a mammal and consists of administering an effective amount of the composition to the mammal. The composition is further useful for preventing fibrin deposition or adhesion formation or reformation.

BRIEF DESCRIPTION OF THE FIGURES

FIG. 2 (parts 1-8). Bivariate histograms for isolation of Mab387 epitope loss mutants. TSA201 cells were transfected and 48 hrs later stained with Mab387 (PE) and Mab372 (FITC). Sort 1 represents the first transfection of the mutagenized K1 library. Cells were sorted that fell within the top left quadrant, along the "diagonal" of expressing cells. Episomal DNA was isolated and retransfected (sort two). Following the second sort, individual clones were analyzed using the 2-color immunofluorescence assay. Shown are a mock transfected control, and histograms for mutants k2, 3, 7, 10 (all epitope loss mutants) and K1-6, which displayed a wild type binding pattern.

FIG. 3. Stereoview of the 3-D mapping of the 387 epitope on t-PA K1. The CA trace is from the X-ray crystal structure of t-PA K2. Sidechain conformations of K1 are based as closely as possible on those from the K2 crystal structure. Sidechains of Asn115, Asn142 and Lys159 are highlighted.

FIG. 4 (parts a-c). Top panel; FITC-t-PA binding to HepG2 cells measured by flow cytometry. Binding is measured as relative fluorescence intensity above autofluorescence. Shown are total binding (●) and specific binding (○) after subtraction of nonspecific binding in the presence of 100 fold molar excess of t-PA. Middle panel; blocking of FITC-t-PA to HepG2 cells by preincubation with the various mutant t-PA's. Cells were pre-incubated with 30 nM mutant t-PA for two hrs, followed by 30 nM FITC t-PA for two hrs. The first two columns show the fluorescence measured with 30 nM FITC-t-PA alone (F) and with a pre-incubation with 30 nM wild type t-PA(wt+F) (+/−SD). Lower panel, clot lysis values for the various mutants relative to control wild type t-PA (+/−SD).

DETAILED DESCRIPTION OF THE INVENTION

I. Definitions

In general, the following words or phrases have the indicated definition when used in the description, examples, and claims.

The terms "t-PA", "human t-PA", and "human tissue plasminogen activator" refer to human extrinsic (tissue-type) plasminogen activator having fibrinolytic activity that typically has a structure with five domains (finger, growth factor, kringle-1, kringle-2, and protease domains), but nonetheless may have fewer domains if it still functions as a thrombolytic agent. At minimum, the t-PA consists of two functional regions consisting of a protease domain that is capable of converting plasminogen to plasmin and an N-terminal region believed to be at least partially responsible for fibrin (ligand) binding. These terms thus include polypeptides containing these functional domains as part of the amino acid sequence of the polypeptide. Biologically active forms of t-PA may be produced by recombinant cell culture systems in forms comprising the two functional regions of the molecule and any other portions of t-PA otherwise native to the source of the t-PA. It will be understood that natural allelic variations exist and can occur among individuals, as demonstrated by one or more amino acid differences in the amino acid sequence of t-PA of each individual.

The terms "wild-type t-PA" and "native t-PA" refer to native sequence human t-PA, i.e., that encoded by the cDNA sequence reported in U.S. Pat. No. 4,766,075. Amino acid site numbers or positions in the t-PA molecule are also labelled in accordance with U.S. Pat. No. 4,766,075. The t-PA may be from any native source and includes the corresponding proteins of various animals such as humans. In addition, the t-PA may be obtained from any recombinant expression system, including, for example, Chinese hamster ovary (CHO cells) or human embryonic kidney 293 cells.

The terms "amino acid" and "amino acids" refer to all naturally occurring L-α-amino acids. The amino acids are identified by either the single-letter or three-letter designations:

Asp D aspartic acid
Thr T threonine
Ser S serine
Glu E glutamic acid
Pro P proline
Gly G glycine
Ala A alanine
Cys C cysteine
Val V valine
Met M methionine
Ile I isoleucine
Leu L leucine
Tyr Y tyrosine
Phe F phenylalanine
His H histidine
Lys K lysine
Arg R arginine
Trp W tryptophan
Gln Q glutamine
Asn N asparagine These amino acids may be classified according to the chemical composition and properties of their side chains. They are broadly classified into two groups, charged and uncharged. Each of these groups is divided into subgroups to classify the amino acids more accurately:

I. Charged Amino Acids

Acidic Residues: aspartic acid, glutamic acid

Basic Residues: lysine, arginine, histidine

II. Uncharged Amino Acids

Hydrophilic Residues: serine, threonine, asparagine, glutamine

Aliphatic Residues: glycine, alanine, valine, leucine, isoleucine

Non-polar Residues: cysteine, methionine, proline

Aromatic Residues: phenylalanine, tyrosine, tryptophan

The terms "alteration", "amino acid sequence alteration", "variant" and "amino acid sequence variant" refer to t-PA molecules with some differences in their amino acid sequences as compared to native t-PA. Ordinarily, the variants will possess at least 80% homology with native t-PA, and preferably, they will be at least about 90% homologous with native t-PA. The amino acid sequence variants of t-PA falling within this invention possess a substitution at one or more positions selected from; 115, 142, and 159 and optionally also substitutions, deletions, and/or insertions at certain other positions.

Substitutional t-PA variants are those that have at least one amino acid residue in the native t-PA sequence removed and a different amino acid inserted in its place at the same position. The substitutions may be single, where only one amino acid in the molecule has been substituted, or they may be multiple, where two or more amino acids have been substituted in the same molecule.

Figure 1:
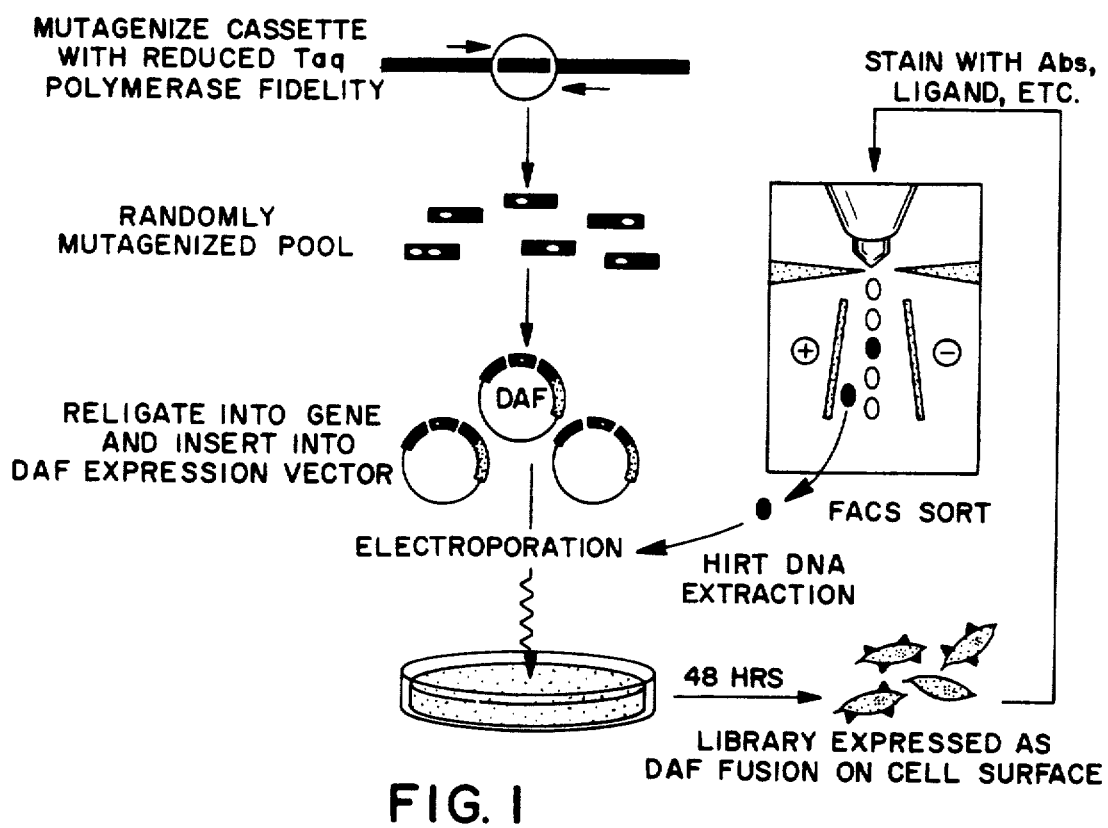
FIG. 1. Scheme for selection of t-PA mutants from randomly mutagenized cDNA libraries using fluorescence activated cell sorting (FACS).
Figure 4A:
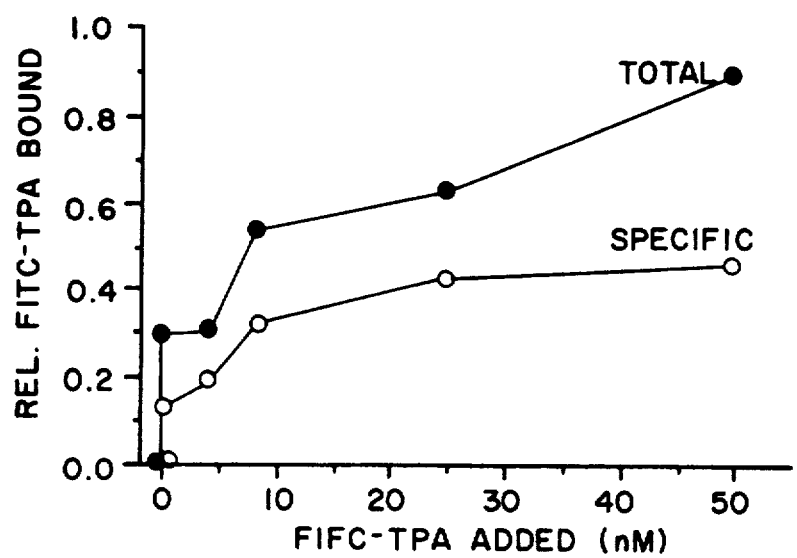
Figure 4B:
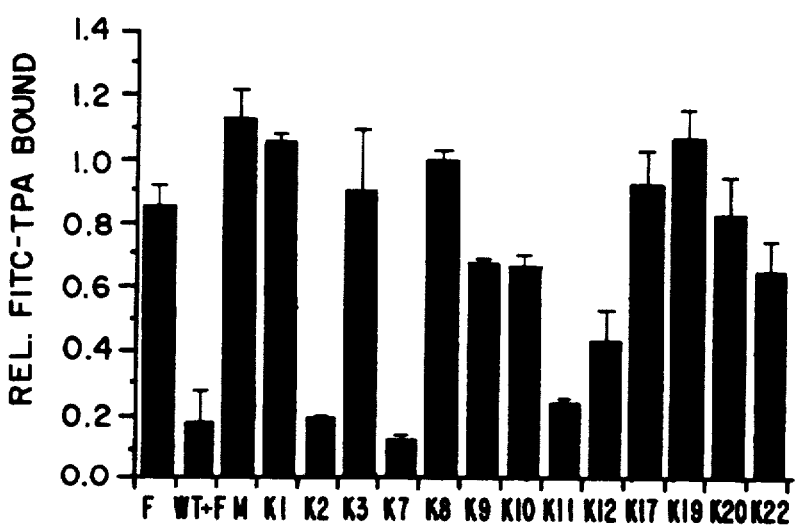
Figure 4C:
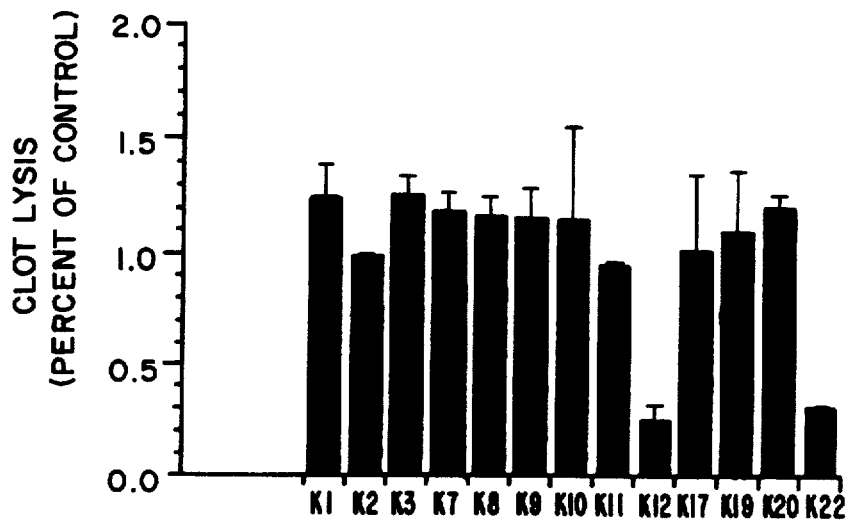

Substantial changes in the activity of the t-PA molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution. Substitutions of this type are preferred in the instant invention in domains or discontinuous epitopes where it is desired to remove or delete an undesired binding property.

Moderate changes in the activity of the t-PA molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional t-PA variants are those with one or more amino acids inserted immediately adjacent to an amino acid at a particular position in the native t-PA molecule. Immediately adjacent to an amino acid means connected to either the a-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those with one or more amino acids in the native t-PA molecule removed. Ordinarily, deletional variants will have one or two amino acids deleted in a particular region of the t-PA molecule. The instant invention contemplates deletion of amino acid residues 115, 142, and/or 159.

The notations used throughout this application to describe t-PA amino acid sequence variants are described below. The location of a particular amino acid in the polypeptide chain of t-PA is identified by a number. The number refers to the amino acid position in the amino acid sequence of the mature, wild-type human t-PA polypeptide as disclosed in U.S. Pat. No. 4,766,075. In the present application, similarly positioned residues in t-PA variants are designated by these numbers even though the actual residue number is not so numbered due to deletions or insertions in the molecule. This will occur, for example, with site-directed deletional or insertional variants. The amino acids are identified using the one-letter code. Substituted amino acids are designated by identifying the wild-type amino acid on the left side of the number denoting the position in the polypeptide chain of that amino acid, and identifying the substituted amino acid on the right side of the number.

For example, replacing the amino acid arginine (K) at position 159 of t-PA with aspartic acid (D) is designated as K159D. Deletional variants are identified by indicating the amino acid residue and position at either end of the deletion, inclusive, and placing the Greek letter delta, "Δ", to the left of the indicated amino acids. For example, a t-PA variant containing a deletion of amino acids 269-299 would be indicated as ΔK296, H297, R298, R299 t-PA, where K, H, and R indicate the amino acids lysine, histidine, and arginine, respectively. Deletion of a single amino acid, for example K159, would be indicated as ΔK159. Insertional t-PA variants are designated by the use of brackets "[]" around the inserted amino acids, and the location of the insertion is denoted by indicating the position of the amino acid on either side of the insertion. For example, an insertion of the amino acid alanine (A) between glutamic acid at position 94 and aspartic acid at position 95 is indicated as E94[A]D95. For ease of reading, a comma "," is used to separate multiple mutations that occur in a single molecule, and a semi-colon "," is used to separate individual t-PA variant molecules that have been constructed, where several t-PA variant molecules are listed together.

"Stringent conditions" are any of those that (1) employ low ionic strength and high temperature for washing, for example, 0.015M NaCl/0.0015M sodium citrate/0.1% $NaDodSO_4$ at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employing 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, then synthetic oligonucleotide adaptors or linkers are used in accord with conventional practice.

An "exogenous" element is defined herein to mean nucleic acid sequence that is foreign to the cell, or homologous to the cell but in a position within the host cell nucleic acid in which the element is ordinarily not found.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Restriction Enzyme Digestion" of DNA refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56-1.61 of Sambrook et al. (*Molecular Cloning: A Laboratory Manual* New York: Cold Spring Harbor Laboratory Press, 1989).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9: 6103-6114 (1981), and Goeddel et al., *Nucleic Acids Res.* 8: 4057 (1980).

"Southern blot analysis" is a method by which the presence of DNA sequences in a restriction endonuclease digest of DNA or DNA-containing composition is confirmed by hybridization to a known, labeled oligonucleotide or DNA fragment. Southern analysis typically comprises electrophoretic separation of DNA digests on agarose gels, denaturation of the DNA after electrophoretic separation, and transfer of the DNA to nitrocellulose, nylon, or another suitable membrane supports for analysis with a radiolabeled, biotinylated or enzyme-labeled probe as described in sections 9.37-9.52 of Sambrook et al, supra.

"Northern analysis" is a method used to identify RNA sequences that hybridize to a known probe such as an oligonucleotide, DNA fragment, cDNA or fragment thereof, or RNA fragment. The probe is labeled with a radioisotope such as 32-P, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39-7.52 of Sambrook et al., supra.

"Ligation" refers to the process of forming phosphodiester bonds between two nucleic acid fragments. To ligate the DNA fragments together, the ends of the DNA fragments must be compatible with each other. In some cases, the ends will be directly compatible after endonuclease digestion. However, it may be necessary to first convert the staggered ends commonly produced after endonuclease digestion to blunt ends to make them compatible for ligation. To blunt the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenolchloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase, or calf intestinal phosphatase to prevent self-ligation during the ligation step.

"Preparation" of DNA from cells means isolating the plasmid DNA from a culture of the host cells. Commonly used methods for DNA preparation are the large and small scale plasmid preparations described in sections 1.25-1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032 published May 4, 1988, or via deoxynucleoside H-phosphonate intermediates as described by Froehler et al., *Nucl. Acids Res.*, 14:5399-5407 [1986]). They are then purified on polyacrylamide gels.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich, ed., *PCR Technology*, Stockton Press, NY, (1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid that is complementary to a particular nucleic acid.

II. Discovery that lead to the Invention

Prior data showed that preincubation of tissue plasminogen activator (t-PA) with monoclonal antibody 387 (Mab387) could partially block t-PA binding to rat hepatocyes. A technique was developed to map a distinct nonlinear region of t-PA important in recognition of antibody 387. In the course of this work novel t-PA mutants possessing specific altered functional properties were isolated from a random polymerase chain reaction (PCR) generated library of mutants. Since t-PA is normally secreted, the expression vector selected and used for screening encoded a t-PA-DAF fusion protein. This construct displayed the library of variant proteins on the surface of transfected mammalian cells. Furthermore, the t-PA-DAF fusion allows phospholipase C cleavage of the fusion protein at the decay acceleration factor (DAF) phosphatidylinositol anchor (Caras, I., et al., *Science* 238:1280–1283 (1987)) for release of biologically active t-PA variants for immediate protein function studies. Expression in mammalian cells was found to be of particular advantage when used to study proteins that require post-translational processing steps for correct glycosylation and conformation, e.g., for proper disulfide bond formation.

Expression of the t-PA-DAF fusion libraries can be screened by any number of approaches known to those skilled in the art. Preferably, fluorescence activated cell sorting (FACS) is used to isolate mutants lacking specific antibody binding determinants while retaining others. The ability to simultaneously measure and sort with two different Mabs by FACS can be used to exclude from analysis and sorting those cells that do not express surface t-PA and those cells that express globally misfolded proteins. This sequence mapping approach can be used to rapidly define regions or domains of structural importance in a protein having discontinuous epitopes. The Mab387 epitope was mapped using the mutants to a discontinuous region that involves residues N115, N142 and K159 of t-PA. By analogy, this technique may be applied to other non-membrane or soluble proteins.

During these studies it was found that for t-PA in general, substitutions in the kringle 1 (K1) domain appeared to have little effect on fibrin clot lysis assay as measured both by plasminogen activation and fibrin binding activities of t-PA. However, it is postulated that large numbers of mutations in any domain may affect activity. Not surprisingly, mutant k12 (see Table 1 of Example II) possessing 10 substitutions in the K1 domain (including two Cys substitutions) was only 20% as active as wild-type t-PA. Mutant k22 also possessed decreased activity compared to wild-type t-PA. This mutant had an N146D mutation in the K1 domain and a L194P mutation in the K2 domain. As N146 is expected to be located in an internal position in the K1 domain, it is conceivable that placement of a charged residue there would grossly disrupt the t-PA structure.

Further research showed that in contrast to the overall lack of effect of K1 substitutions on clot lysis activity, substitutions in the K1 domain appeared to have marked effects on the ability of the mutants to bind to the t-PA receptor expressed in HepG2 cells. All of the mutants with changes in the Mab387 epitope that involves amino acids N142, N115 and K159 also had reduced binding to the t-PA receptor as compared to wild-type t-PA. It is contemplated that t-PA with mutations, including deletions, in these three residues will possess a longer half life in vivo. Using domain deletion mutants, previous investigators have shown that in vivo clearance is decreased by deletion of the finger and growth factor domains (Collen, D., et al., *Blood* 71:216–219 [1988] and Kaylan, N., et al., *J. Biol. Chem.* 263:3971–3978 [1988]) or removal of glycosylation sites (Kaylan supra).

In summary, it has been discovered that PCR/FACS random mutagenesis and cell sorting methodology using a vector containing a membrane anchor polypeptide linked to a protein that is normally secreted permits rapid sorting of secreted proteins directly by expression in mammalian cells. A method for screening randomly mutagenized expression libraries in mammalian cells using fluorescence activated cell sorting (FACS) was developed. The cDNA sequence of a secreted protein was randomly mutagenized using polymerase chain reaction (PCR) under conditions of reduced Taq polymerase fidelity. The mutated DNA was inserted into an expression vector encoding the membrane glycophospholipid anchor sequence of decay acceleration factor (DAF) fused to the carboxyl terminus of the secreted protein. This resulted in the expression of the chimeric protein on the cell surface in transiently transfected mammalian cells, which were then be screened using FACS. This method was used to isolate mutants in the Kringle 1 (K1) domain of tissue plasminogen activator (t-PA) that were no longer be recognized by a specific monoclonal antibody (Mab387) that inhibits the binding of t-PA to its clearance receptor. DNA sequence analysis of the mutants and the localization of the mutated residues on a three-dimensional model of the K1 domain identified three key amino acid residues that were essential for Mab387 binding. Mutants with changes in any of these three residues were found to have reduced binding to the t-PA receptor on human hepatoma HepG2 cells but to retain full clot lysis activity. The method is useful for mapping nonlinear (i.e. discontinuous epitope) structural domains involved in antibody binding as well as functional properties that are associated with antibody binding to the molecule. Several minimally substituted K1 domain t-PA mutants were isolated having decreased ability to bind to the putative hepatic t-PA clearance receptor in vitro.

This discovery led to the development of a general method for screening randomly mutagenized expression libraries in mammalian cells using fluorescence activated cell sorting (FACS) to obtain other amino acid sequence variant proteins with altered binding properties.

III. Preferred Embodiments

1. Choice of Proteins for Display on the Surface of a Cell

The first step in the method of this invention is to choose a wild-type protein having rigid secondary structure presented on the surface of the protein for display on the surface of a cell.

By "protein" as used herein is meant any molecule whose expression can be directed by a specific DNA sequence.

By "rigid secondary structure" as used herein is meant any polypeptide segment exhibiting a regular repeated structure such as is found in; α-helices, $3_{10}$ helices, π-helices, parallel and antiparallel β-sheets, and reverse turns. Certain "non-ordered" structures that lack recognizable geometric order are also included in the definition of rigid secondary structure provided they form a domain or "patch" of amino acid residues capable of interaction with a reporter molecule and that the overall shape of the structure is not destroyed by replacement of an amino acid at a second site or domain within the molecule. It is believed that some non-ordered structures are combinations of reverse turns. The geometry of these rigid secondary structures is well defined by $\phi$ and $\psi$ torsional angles about the α-carbons of the peptide "backbone".

The requirement that the secondary structure be exposed to the surface of the protein is to provide a domain or "patch" of amino acid residues that can be exposed to and bind with a first reporter molecule. Typically this first reporter molecule will bind to the wild-type protein and to the variant protein with substantially the same affinity. The protein will also have a second domain or patch displayed on the surface recognizable by a second reporter molecule. It is primarily amino acid residues within this second domain that are replaced by mutagenesis that form the "library" of structurally related (mutant or variant) binding proteins that are displayed on the surface of the mammalian cell from which proteins having novel structure and properties are selected. Typically, the second reporter molecule will fail to bind to "properly" mutated variant proteins (i.e. those lacking an undesired property) and this lack of binding will be used to select (i.e. by cell sorting) variants having desired properties.

Mutagenesis or replacement of amino acid residues directed toward the interior of the polypeptide is generally avoided so that the overall structure of the rigid secondary structure is preserved. Some replacement of amino acids on the interior region of the rigid secondary structures, especially with hydrophobic amino acid residues, may be tolerated since these conservative substitutions are unlikely to distort the overall structure of the polypeptide. Conversely, some distortion of the secondary structure by mutagenesis in a domain that contains the "undesired" property may also be tolerated provided the "desired" property is not adversely affected.

From the forgoing it will be appreciated that the amino acid residues that form the binding domain of the polypeptide will not be sequentially linked. That is, the binding domain tracks with the particular secondary and tertiary structure at the binding site and not the primary structure. Thus, optionally, mutations will be introduced into codons encoding amino acids within a particular secondary structure at sites directed away from the interior of the polypeptide so that they will have the potential to interact with the reporter molecules.

This invention contemplates any mutant of a wild-type protein that binds to one or more reporter molecules, and includes antibodies. Preferred proteins are those that have pharmaceutical utility. More preferred polypeptides include; a growth hormone, including human growth hormone, des-N-methionyl human growth hormone, and bovine growth hormone; parathyroid hormone; thyroid stimulating hormone; thyroxine; insulin A-chain; insulin B-chain; proinsulin; follicle stimulating hormone; calcitonin; leutinizing hormone; glucagon; factor VIII; an antibody; lung surfactant; a plasminogen activator, such as urokinase or human tissue-type plasminogen activator (t-PA); bombesin; factor IX, thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as β-lactamase; tissue factor protein; inhibin; activin; vascular endothelial growth factor; receptors for hormones or growth factors; integrin; thrombopoietin; protein A or D; rheumatoid factors; nerve growth factor such as NGF-β; platelet-derived growth factor; fibroblast growth factor such as αFGF and βFGF; epidermal growth factor; transforming growth factor (TGF) such as TGF-α and TGF-β; insulin-like growth factor-I and -II; insulin-like growth factor binding proteins; CD-4; DNase; latency associated peptide; erythropoietin; osteoinductive factors; an interferon such as interferon-alpha, -beta, and -gamma; colony stimulating factors (CSFs), e.g., M-CSF, GM-CSF, and G-CSF; interleukins (ILs), e.g., IL-1, IL-2, IL-3, IL-4, etc.; superoxide dismutase; viral antigen such as, for example, a portion of the HIV envelope; immunoglobulins; and fragments of any of the above-listed polypeptides. In addition, one or more predetermined amino acid residues on the polypeptide may be substituted, inserted, or deleted, for example, to produce products with improved biological properties. Further, fragments of these polypeptides, especially biologically active fragments, are included. Yet more preferred polypeptides of this invention are t-PA, human growth hormone, and atrial naturetic peptides A, B, and C, endotoxin, subtilisin, trypsin and other serine proteases.

Still other preferred proteins are protein hormones that can be defined as any amino acid sequence produced in a first cell that binds specifically to a receptor on the same cell type (autocrine hormones) or a second cell type (non-autocrine) and causes a physiological response characteristic of the receptor-bearing cell. These proteins are generally referred to as secretory proteins. Among such protein hormones are cytokines, lymphokines, neurotrophic hormones and adenohypophyseal polypeptide hormones such as growth hormone, prolactin, placental lactogen, luteinizing hormone, follicle-stimulating hormone, thyrotropin, chorionic gonadotropin, corticotropin, α or β-melanocyte-stimulating hormone, β-lipotropin, γ-lipotropin and the endorphins; hypothalmic release-inhibiting hormones such as corticotropin-release factor, growth hormone release-inhibiting hormone, growth hormone-release factor; and other polypeptide hormones such as atrial natriuretic peptides A B or C.

II. Isolation of DNA Encoding the Desired (wild-type) Protein

The DNA encoding the desired protein may be obtained from any cDNA library prepared from tissue believed to possess the desired protein mRNA and to express it at a detectable level. The desired protein gene may also be obtained from a genomic library.

Libraries are screened with probes designed to identify either DNA encoding or the desired protein, or the desired protein itself. For cDNA expression libraries, suitable probes include monoclonal or polyclonal antibodies that recognize and specifically bind to the desired protein; oligonucleotides of about 20–80 bases in length that encode known or suspected portions of the desired protein cDNA from the same or different species; and/or complementary or homologous cDNAs or fragments thereof that encode the same or a similar gene. Appropriate probes for screening genomic DNA libraries include, but are not limited to, oligonucleotides; cDNAs or fragments thereof that encode the same or a similar gene; and/or homologous genomic DNAs or fragments thereof. Screening the cDNA or genomic library with the selected probe may be conducted using standard procedures as described in chapters 10–12 of Sambrook et al., supra.

An alternative means to isolate the gene encoding desired protein is to use polymerase chain reaction (PCR) methodology as described in section 14 of Sambrook et al., supra. This method requires the use of oligonucleotide probes that will hybridize to the desired protein. Strategies for selection of oligonucleotides are described below.

Another alternative method for obtaining the gene encoding the desired protein is to chemically synthesize it using one of the methods described in Engels et al. (*Agnew. Chem. Int. Ed. Engl.*, 28: 716-734 [1989]). These methods include triester, phosphite, phosphoramidite and H-Phosphonate methods, PCR and other autoprimer methods, and oligonucleotide syntheses on solid supports. These methods may be used if the entire nucleic acid sequence of the gene is known, or the sequence of the nucleic acid complementary to the coding strand is available, or alternatively, if the target amino acid sequence is known, one may infer potential nucleic acid sequences using known and preferred coding residues for each amino acid residue.

A preferred method of practicing this invention is to use carefully selected oligonucleotide sequences to screen cDNA libraries from various mammalian tissues.

The oligonucleotide sequences selected as probes should be of sufficient length and sufficiently unambiguous that false positives are minimized. The actual nucleotide sequence(s) is usually based on conserved or highly homologous nucleotide sequences or regions of other proteins structurally related to the desired protein. The oligonucleotides may be degenerate at one or more positions. The use of degenerate oligonucleotides may be of particular importance where a library is screened from a species in which preferential codon usage in that species is not known. The oligonucleotide must be labeled such that it can be detected upon hybridization to DNA in the library being screened. The preferred method of labeling is to use 32-P labeled ATP with polynucleotide kinase, as is well known in the art, to radiolabel the oligonucleotide. However, other methods may be used to label the oligonucleotide, including, but not limited to, biotinylation or enzyme labeling.

Of particular interest is the desired protein nucleic acid that encodes the full-length desired protein. For some desired proteins, this will include the signal sequence. Nucleic acid having all the protein coding sequence is obtained by screening selected cDNA or genomic libraries, and, if necessary, using conventional primer extension procedures as described in section 7.79 Sambrook et al., supra, to detect precursors and processing intermediates of mRNA that may not have been reverse-transcribed into cDNA.

III. Producing Amino Acid Sequence Variants of the (Wild-type) Desired Protein

Amino acid sequence variants of the desired protein may be prepared by random mutagenesis of DNA corresponding to a particular domain or region of the wild-type protein using PCR conditions of reduced Taq polymerase fidelity, as described in Example I. Many other mutagenesis techniques, more or less random in nature, may optionally be used to obtain a similar result. Some of these techniques are briefly described below, however, it will be appreciated that alternative procedures may produce an equivalent result. These techniques may be used to create the initial library of related variant DNA molecules or for producing variants based on an analysis of the DNA sequence of the variants obtained by biological selection, i.e. cell sorting.

Amino acid sequence variants of the desired protein may be prepared by introducing appropriate nucleotide changes into the desired protein DNA, or by in vitro synthesis of the desired desired protein. Such variants include, for example, deletions from, or insertions or substitutions of, residues within the known amino acid sequence of the desired protein. Any combination of deletion, insertion, and substitution can be made to arrive at the final construct, provided that the final construct possesses the desired binding properties or characteristics. The amino acid changes also may alter post-translational processes of the desired protein, such as changing the number or position of glycosylation sites, and/or altering the intracellular location of the desired protein by inserting, deleting, or otherwise affecting the leader sequence of the desired protein.

In designing amino acid sequence variants of the desired protein, the location of the mutation site and the nature of the mutation will depend on the desired protein binding characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1-3.

A useful method for identification of certain residues or regions of the desired protein that are preferred locations or domains for mutagenesis, called "alanine scanning mutagenesis", is described by Cunningham and Wells (*Science*, 244: 1081-1085 [1989]). Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, Ala scanning or random mutagenesis may be conducted at the target codon or region and the expressed desired protein subunit variants are screened for the optimal combination of desired activity.

Amino acid sequence deletions generally range from about 1 to 30 residues, more preferably about 1 to 10 residues. Deletions may be introduced into regions of low homology between the desired protein and similar proteins to modify the activity of the desired protein. Deletions from the desired protein in areas of substantial homology with a similar desired protein will be more likely to modify the biological activity of the desired protein more significantly. The number of consecutive deletions will be selected so as to preserve the tertiary structure of desired protein in the affected domain, e.g., $\beta$-pleated sheet or $\alpha$-helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the desired protein) may range generally from about 1 to 10 residues, more preferably 1 to 5, most preferably 1 to 3.

Other insertional variants of the desired protein include the fusion to the N-or C-terminus of the desired protein of immunogenic polypeptides, e.g., bacterial polypeptides such as $\beta$-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published Apr. 6, 1989. Fusion of the desired protein to a membrane anchor domain polypeptide is discussed in detail below.

In another embodiment, any methionyl residues other than the starting methionyl residue of the signal sequence, or any residue located within about three residues N- or C-terminal to each such methionyl residue, is substituted by another residue or deleted. Alternatively, about 1–3 residues are inserted adjacent to such sites.

Any cysteine residues not involved in maintaining the proper conformation of desired protein also may be substituted, generally with serine, to improve the oxidative stability of the molecule and prevent aberrant crosslinking. DNA encoding amino acid sequence variants of the desired protein are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and/or cassette mutagenesis of an earlier prepared variant or a non-variant version of the desired protein. These techniques may utilized desired protein nucleic acid (DNA or RNA), or nucleic acid complementary to the desired protein nucleic acid.

Oligonucleotide-mediated mutagenesis is a suitable method for preparing substitution, deletion, and insertion variants of desired protein DNA. This technique is well known in the art as described by Adelman et al., *DNA*, 2: 183 (1983). Briefly, the desired protein DNA is altered by hybridizing an oligonucleotide encoding the desired mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA*, 75: 5765 [1978]).

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the desired protein, and the other strand (the original template) encodes the native, unaltered sequence of the desired protein subunit. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host. The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM101, as described above.

DNA encoding the desired protein mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also a suitable and preferred method for making amino acid variants of desired protein. The PCR technique generally refers to the following procedure (see Erlich, supra, the chapter by R. Higuchi, p. 61-70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide tri-phosphates and is included in the GeneAmp ® kits (obtained from Perkin-Elmer Cetus, Norwalk, Conn. and Emeryville, Calif.), and 25 pmole of each oligonucleotide primer, to a final volume of 50 μl. The reaction mixture is overlaid with 35 μl mineral oil. The reaction is denatured for 5 minutes at 100° C., placed briefly on ice, and then 1 μl *Thermus aquaticus* (Taq) DNA polymerase (5 units/μl, purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C.,
30 sec. 72° C., then 19 cycles of the following:
30 sec. 94° C.,
30 sec. 55° C., and
30 sec. 72° C.

At the end of the program, the reaction vial is removed from the thermal cycler and the aqueous phase transferred to a new vial, extracted with phenol/-chloroform (50:50:vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al. (*Gene*, 34:315 [1985]). The starting material is the plasmid (or other vector) comprising the desired protein subunit DNA to be mutated. The codon(s) in the desired protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated desired protein subunit DNA sequence.

IV. Formation of the Membrane Anchor-Variant Protein Gene Fusion

This invention contemplates producing novel proteins by fusing a membrane anchor polypeptide with a variant of the desired protein. The membrane anchor polypeptide will typically be a particular hydrophobic fragment of an integral membrane protein, namely the membrane spanning domain fragment. For use herein, the membrane anchor polypeptide can be obtained from any integral membrane-bound protein in any organism, provided that the polypeptide is capable of functioning as an anchor to hold the desired protein to which it is fused in the plasma membrane of the host cell. It is also contemplated that non-naturally-occurring membrane anchor polypeptides may be suitable provided the amino acid residues are of the proper character (primarily hydrophobic) and length (sufficient to span the cell membrane i.e. at least about 20 residues) and contain an anchoring group (i.e. typically a charged region near the carboxy terminus). A preferred membrance anchor polypeptide is that obtained from the eukaryotic protein decay accelerating factor (DAF).

The DNA encoding the membrane anchor polypeptide can be obtained using any of the methods described in the previous section for isolation of the DNA encoding the desired protein. Normally, the amino acid sequence, and usually the DNA sequence as well, will be known. Thus, the precise location of the DNA encoding only the membrane anchor domain of the integral membrane protein can be determined, and this fragment can be excised by using appropriate restriction endonucleases.

A satisfactory and convenient alternative method for obtaining the DNA encoding the membrane anchor polypeptide is to chemically synthesize the DNA using methods described above.

The DNA encoding the membrane anchor polypeptide will typically be fused to the DNA encoding the mutant desired protein such that the 3' end of the DNA encoding the desired protein is fused to the 5' end of the DNA encoding the membrane anchor polypeptide. The resulting fusion protein will thus have the mutant desired protein as the amino-terminal portion of the fusion, and the membrane anchor polypeptide as the carboxyl terminal portion of the fusion protein. As such, the mutant desired protein will be directed to the outside of the cell, but will be anchored on to the cell surface by the membrane anchor polypeptide portion of the fusion protein.

The DNA encoding the membrane anchor polypeptide can be attached to the DNA encoding the mutant desired protein using standard ligation techniques well known in the art and as described above. In some cases, it will be more convenient to first ligate the DNA encoding only the membrane anchor polypeptide directly into the vector that will be used to transform the host cells. The mutated desired protein DNA can then subsequently be ligated into this vector in the proper orientation such that the 5' end of the DNA encoding the membrane anchor polypeptide is ligated to the 3' end of the DNA encoding the desired protein. To accomplish the ligation and to create a fusion protein that will be in the proper reading frame, it may be necessary to use linkers or to otherwise alter the ends of the DNAs to be ligated. The necessary manipulation will readily be apparent to those of ordinary skill in the art.

An alternative means of creating the fusion protein is to first ligate the DNA encoding the membrane anchor polypeptide to the DNA encoding the desired polypeptide such that a fusion DNA is created. This is accomplished using standard techniques well known in the art. The fusion DNA can then be inserted into the vector that has been selected to transform the host cells.

V. Insertion of DNA into a Cloning Vehicle

The cDNA or genomic DNA encoding the fusion protein is inserted into a replicable vector for further cloning (amplification of the DNA) or for expression. Insertion is readily accomplished using standard ligation procedures well known in the art. Prior to ligation however the ends of the DNA to be ligated must be made compatible.

Many vectors are available, and selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence. The various components of the vector are ligated together in the desired order, using standard techniques known in the art such as described in section 1.63-1.70 of Sambrook et al., supra.

(i) Signal Sequence Component

A signal sequence will frequently be necessary for practicing this invention. In general, the signal sequence may be a component of the vector, or it may be a part of the desired protein DNA that is inserted into the vector. In some cases, the native desired protein DNA may encode a signal sequence at the amino terminus (5' end of the DNA) of the protein that is normally cleaved during post-translational processing of the protein to form the mature desired protein.

The desired protein of this invention is expressed as a fusion with a membrane anchor domain polypeptide which prevents the desired protein from being secreted. In general, the signal sequence may be a component of the vector, or it may be a part of the desired protein DNA that is inserted into the vector. Included within the scope of this invention are desired proteins with the native signal sequence deleted and replaced with a heterologous signal sequence. The heterologous signal sequence selected should be one that is recognized and processed (i.e. cleaved by a signal peptidase) by the host cell. For prokaryotic host cells that do not recognize and process the native desired protein subunit signal sequence, the signal sequence is substituted by a prokaryotic signal sequence selected, for example, from the group of the alkaline phosphatase, penicillinase, 1 pp, or heatstable enterotoxin II leaders. For yeast secretion the native desired protein signal sequence may be substituted by the yeast invertase, alpha factor, or acid phosphatase leaders. In mammalian cell expression the native signal sequence is satisfactory, although other mammalian signal sequences may be suitable.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in E. coli and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the desired protein subunit DNA. However, the recovery of genomic DNA encoding the desired protein is more complex than that of an exogenously replicated vector because restriction enzyme digestion is required to excise the desired protein DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.*, 1: 327 [1982]), mycophenolic acid (Mulligan et al., *Science*, 209: 1422 [1980]) or hygromycin (Sugden et al., *Mol. Cell. Biol.*, 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the desired protein subunit nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the desired protein subunit. Amplification is the process by which genes in greater demand for the production of a protein critical for growth are reiterated in tandem within the chromosomes of successive generations of recombinant cells. Increased quantities of the desired protein are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the desired protein. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the desired protein, wild-type DHFR protein, and another selectable marker such as aminoglycoside 3' phosphotransferase (APH) can be selected by cell growth in medium containing a selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282: 39 [1979]; Kingsman et al., *Gene*, 7: 141 [1979]; or Tschemper et al., *Gene*, 10: 157 [1980]). The trp1 gene provides a selection marker for a mutant strain of yeast lacking the ability to grow in tryptophan, for example, ATCC No. 44076 or PEP4-1 (Jones, *Genetics*, 85: 12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression and cloning vectors usually contain a promoter that is recognized by the host organism and is operably linked to the desired protein nucleic acid. Promoters are untranslated sequences of nucleic acid that are located upstream (5') to the start codon of a structural gene (generally within about 100 to 1000 bp) that control the transcription and translation of a particular nucleic acid sequence to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the desired protein by removing the promoter from the source DNA by restriction enzyme digestion and inserting the isolated promoter sequence into the vector. Both the native desired protein subunit promoter sequence and many heterologous promoters may be used to direct amplification and/or expression of the desired protein DNA. However, heterologous promoters are preferred, as they generally permit greater transcription and higher yields of expressed desired protein subunit as compared to the native desired protein subunit promoter.

Promoters suitable for use with prokaryotic hosts include the β-lactamase and lactose promoter systems (Chang et al., *Nature*, 275: 615 [1978]; and Goeddel et al., *Nature*, 281: 544 [1979]), alkaline phosphatase, a tryptophan (trp) promoter system (Goeddel, *Nucleic Acids Res.*, 8: 4057 [1980] and EP 36,776) and hybrid promoters such as the tac promoter (deBoer et al., *Proc. Natl. Acad. Sci. USA*, 80: 21-25 [1983]). However, other known bacterial promoters are suitable. Their nucleotide sequences have been published, thereby enabling a skilled worker operably to ligate them to DNA encoding the desired protein (Siebenlist et al., *Cell*, 20: 269 [1980]) using linkers or adaptors to supply any required restriction sites. Promoters for use in bacterial systems also generally will contain a Shine-Dalgarno (S.D.) sequence operably linked to the DNA encoding the desired protein.

Suitable promoting sequences for use with yeast hosts include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; and Holland, *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

Desired protein transcription from vectors in mammalian host cells is controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the promoter normally associated with the desired protein sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273: 113 (1978); Mulligan and Berg, *Science*, 209: 1422-1427 (1980); Pavlakis et al., *Proc. Natl. Acad. Sci. USA*, 78: 7398-7402 (1981). The immediate early promoter of the human cytomegalovirus is conveniently obtained as a Hind III restriction fragment. (Greenaway et al., *Gene*, 18: 355-360 [1982]). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503-508 (1982) on expressing cDNA encoding immune interferon in monkey cells;. Reyes et al., *Nature*, 297: 598-601 (1982) on expression of human γ-interferon cDNA in mouse cells under the control of a thymidine kinase promoter from herpes simplex virus, Canaani and Berg, *Proc. Natl. Acad. Sci. USA*, 79: 5166-5170 (1982) on expression of the human interferon 1 gene in cultured mouse and rabbit cells, and Gorman et al., *Proc. Natl. Acad. Sci. USA*, 79: 6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the desired protein of this invention by higher eukaryotes may be increased by inserting an enhancer sequence into the vector. Enhancers are cis-acting elements of DNA, usually about from 10-300 bp, that act on a promoter to increase its transcription. Enhancers are relatively orientation and position independent having been found 5' (Laimins et al., *Proc. Natl. Acad. Sci. USA*, 78: 993 [1981]) and 3' (Lusky et al., *Mol. Cell Bio.*, 3: 1108 [1983]) to the transcription unit, within an intron (Banerji et al., *Cell*, 33: 729 [1983]) as well as within the coding sequence itself (Osborne et al., *Mol. Cell Bio.*, 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature*, 297: 17-18 (1982) on enhancing elements for activation of eukaryotic promoters. The enhancer may be spliced into the vector at a position 5' or 3' to the desired protein subunit DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the desired protein subunit. The 3' untranslated regions also include transcription termination sites.

Construction of suitable vectors containing one or more of the above listed components the desired coding and control sequences employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65: 499 (1980).

Particularly useful in the practice of this invention are expression vectors that provide for the transient expression in mammalian cells of DNA encoding the desired protein. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of the desired protein that have desired protein activity.

Other methods, vectors, and host cells suitable for adaptation to the synthesis of the desired protein subunit in recombinant vertebrate cell culture are described in Gething et al., *Nature*, 293: 620–625 [1981]; Mantei et al., *Nature*, 281: 40–46 [1979]; Levinson et al.; EP 117,060; and EP 117,058. A particularly useful plasmid for mammalian cell culture expression of the desired protein subunit is the pRK5 vector (EP pub. no. 307,247) or the pSVI6B vector (U.S. Ser. No. 07/441,574 filed Nov. 22, 1989, the disclosure of which is incorporated herein by reference).

VI. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli*, Bacilli such as *B. subtilis*, Pseudomonas species such as *P. aeruginosa*, *Salmonella typhimurium*, or *Serratia marcescans*. One preferred *E. coli* cloning host is *E. coli* 294 (ATCC 31,446), although other strains such as *E. coli* B, *E. coli* 1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g. PCR or other nucleic acid polymerase reactions, are suitable.

In addition to prokaryotes, eukaryotic microbes such as filamentous fungi or yeast are suitable hosts for desired protein-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* [Beach and Nurse, *Nature*, 290: 140 (1981); EP 139,383 published May 2, 1985], Kluyveromyces hosts (U.S. Pat. No. 4,943,529) such as, e.g., *K. lactis* [Louvencourt et al., *J. Bacteriol.*, 737 (1983)], *K. fragilis*, *K. bulgaricus*, *K. thermotolerans*, and *K. marxianus*, yarrowia [EP 402,226], *Pichia pastoris* [EP 183,070; Sreekrishna et al., *J. Basic Microbiol.*, 28: 265–278 (1988)], Candida, *Trichoderma reesia* [EP 244,234], *Neurospora crassa* [Case et al., *Proc. Natl. Acad. Sci. USA*, 76: 5259–5263 (1979)], and filamentous fungi such as, e.g., Neurospora, Penicillium, Tolypocladium [WO 91/00357 published Jan. 10, 1991], and Aspergillus hosts such as *A. nidulans* [Ballance et al., *Biochem. Biophys. Res. Commun.*, 112: 284–289 (1983); Tilburn et al., *Gene*, 26: 205–221 (1983); Yelton et al., *Proc. Natl. Acad. Sci. USA*, 81: 1470–1474 (1984)] and *A. niger* [Kelly and Hynes, *EMBO J.*, 4: 475–479 (1985)].

Suitable host cells for the expression of a glycosylated desired protein is derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., *Bio/Technology*, 6: 47–55 (1988); Miller et al., in *Genetic Engineering*, Setlow, J. K. et al., eds., Vol. 8 (Plenum Publishing, 1986), pp. 277–279; and Maeda et al., *Nature*, 315: 592–594 (1985). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the desired protein DNA. During incubation of the plant cell culture with *A. tumefaciens*, the DNA encoding desired protein is transferred to the plant cell host such that it is transfected, and will, under appropriate conditions, express the desired protein DNA. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen. Virol.*, 36: 59 [1977]); baby hamster kidney cells (BHK, ATCC CCL 10); Chinese hamster ovary cells/-DHFR (CHO, Urlaub and Chasin, *Proc. Natl. Acad. Sci. USA*, 77: 4216 [1980]); mouse sertoli cells (TM4, Mather, *Biol. Reprod.*, 23: 243-251 [1980]); monkey kidney cells (CV1 ATCC CCL 70); African green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL 51); TRI cells (Mather et al., *Annals N.Y. Acad. Sci.*, 383: 44-68 [1982]); MRC 5 cells; FS4 cells; and a human hepatoma cell line (Hep G2). A preferred cell line is HEK293 and related cell lines.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or after integration into the host chromosome. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published Jun. 29, 1989. For mammalian cells without such cell walls, the calcium phosphate precipitation method described in sections 16.30-16.37 of Sambrook et al, supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci.* (USA), 76: 3829 (1979). However, other methods for introducing DNA into cells such as by nuclear injection, electroporation, or protoplast fusion may also be used.

VII. Culturing the Host Cells

Prokaryotic cells used to produce the desired protein of this invention are cultured in suitable media as described generally in Sambrook et al., supra.

The mammalian host cells used to produce the desired protein of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. Nos. 4,767,704; 4,657,866; 4,927,762; or 4,560,655; WO 90/03430; WO 87/00195; U.S. Pat. Re. 30,985; or copending U.S. Ser. No. 07/592,107 or 07/592,141, both filed in Oct. 3, 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin TM drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that the desired protein of this invention may be produced by homologous recombination, or with recombinant production methods utilizing control elements introduced into cells already containing DNA encoding the desired protein currently in use in the field. For example, a powerful promoter/enhancer element, a suppressor, or an exogenous transcription modulatory element is inserted in the genome of the intended host cell in proximity and orientation sufficient to influence the transcription of DNA encoding the desired protein. The control element does not encode the desired protein of this invention, but the DNA is present in the host cell genome. One next screens for cells making the desired protein of this invention, or increased or decreased levels of expression, as desired.

VIII. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77: 5201-5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like.

Antibodies useful for immunohistochemical staining and/or assay of sample fluids may be either monoclonal or polyclonal, and may be prepared in any mammal. Conveniently, the antibodies may be prepared against a native desired protein subunit polypeptide or against a synthetic peptide based on the DNA sequences provided herein as described further in Section 4 below.

IX. Purification of the Fusion Protein

In some cases, the desired protein fused to the membrane anchor domain polypeptide may be isolated and purified. When the membrane anchor domain polypeptide is DAF, treatment of the cells with phospholipase C will result in release of the fusion protein from the cell membrane. This fusion protein can then be recovered from the cell culture medium. As a first step, the culture medium is centrifuged to remove particulate cell debris. The membrane and soluble protein fractions are then separated by higher speed centrifugation. The desired protein may then be purified from the soluble protein fraction. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG.

Desired protein variants in which residues have been deleted, inserted or substituted are recovered in the same fashion as the native desired protein, taking account of any substantial changes in properties occasioned by the variation. For example, preparation of a desired protein fusion with another protein or polypeptide, e.g. a bacterial or viral antigen, facilitates purification; an immunoaffinity column containing antibody to the antigen can be used to adsorb the fusion. Immunoaffinity columns such as a rabbit polyclonal anti-desired protein column can be employed to absorb the desired protein variant by binding it to at least one remaining immune epitope. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native desired protein may require modification to account for changes in the character of the desired protein or its variants upon expression in recombinant cell culture.

X. Preparing a Reporter Molecule and Binding with Cells Expressing the Chimeric Fusion Protein variant Reporter molecules comprise molecules such as protein ligands, soluble receptors, antibodies and fragments thereof that may be isolated from natural sources or prepared by recombinant methods using procedures known in the art. Protein ligands will generally be the naturally-occurring binding partners of the desired wild-type protein. Thus, for example, they may be naturally occurring variant, or synthetic cell surface receptors, capable of binding with the desired wild-type protein. By way of illustration, soluble glycoprotein hormone receptors may be prepared by the technique described by McFarland et al., Science 245: 494-499 [1989]. Other soluble receptors can be prepared by art standard methods. Antibodies, especially monoclonal antibodies, specific for a particular desired wild-type protein are prepared using standard hybridoma technology by methods known in the art and originally described by Köhler and Milstein, Nature, 256: 495 (1975) (See also U.S. Pat. Nos. 4,172,124 to Koprowski and 4,444,744 to Goldenberg).

The reporter molecule will typically contain a detectable marker such as a fluorophore or other detectable group (see e.g. U.S. Pat. No. 4,444,744 to Goldenberg) covalently linked thereto. Also typically the reporter molecules will simply be contacted with the library of variant chimeric proteins immobilized on the cell (mammalian) surface under conditions known to cause binding of the reporter molecule(s) to the wild-type protein. Cells are then sorted according to a predetermined reporter molecule binding pattern. Typically, each reporter molecule will contain a different detectable marker to facilitate cell sorting. Cells can then be sorted based on either binding or nonbinding with a particular reporter to select for specific desired binding properties.

Optionally, the purified reporter molecule(s) may be attached to and immobilized on a suitable matrix such as agarose beads, acrylamide beads, glass beads, cellulose, various acrylic copolymers, hydroxylalkyl methacrylate gels, polyacrylic and polymethacrylic copolymers, nylon, neutral and ionic carriers, and the like. Attachment of the reporter molecule to the matrix may be accomplished by methods described in Methods in Enzymology, 44: [1976], or by other means known in the art. After attachment of the reporter molecule to the matrix, the immobilized reporter is contacted with the library of chimeric variants under conditions suitable for binding of at least a portion of the variant molecules with the immobilized reporter. Normally, the conditions, including pH, ionic strength, temperature and the like will mimic physiological conditions. When this option is employed it is unnecessary for the reporter molecule to contain a detectable marker, rather, cells will sorted according to a particular elution profile.

Bound cells ("binders") having high affinity for the immobilized reporters are separated from those having a low affinity (and thus do not bind to the reporter) by washing. Binders may be dissociated from the immobilized reporter by a variety of methods. These methods include competitive dissociation using the wild-type ligand, altering pH and/or ionic strength, and methods known in the art.

Suitable cells from the previous step, either binders or non-binders are collected and the selection process is repeated one or more times with other reporter molecules until binders having the desired affinity pattern for the reporter molecule are selected.

XI. t-PA Amino Acid Sequence Variants

The method of this invention has been used thus far to discover three amino acid residues in the K1 domain involved in the binding of a specific reporter molecule (Mab387) capable of interfacing with t-PA binding to the clearance receptor. These residues are N115, N142, and K159. Thus it is contemplated that deletion, substitution or otherwise mutating or derivatizing these residues will modulate the affinity of a t-PA molecule for its clearance receptor. It is further contemplated that mutating other amino acid residues within the same rigid secondary structure(s) as residues N115, N142, and K159 so as to disrupt the secondary structure will likewise modulate the affinity of t-PA for the clearance receptor. Accordingly, preferred t-PA variants will include any amino acid residue other than the wild-type residue at position 115, 142, and 159. More preferred t-PA amino acid sequence variants are substitutions at residues 115 and 142 that are substitutions with charged residues, aliphatic residues, aromatic residues, and nonpolar residues and substitutions at residue 159 that are substitutions with acidic residues and uncharged residues.

EXAMPLES

Without further description, it is believed that one of ordinary skill in the art can, using the preceding description and illustrative examples, make and utilize the present invention to the fullest extent. The following working examples therefore specifically point out preferred embodiments of the present invention, and are not to be construed as limiting in any way of the remainder of the disclosure.

EXAMPLE I

Mutagenesis and Library Screening

In order to screen for K1 domain mutants of t-PA that would no longer bind to Mab387, the expression plasmid, pRK-t-PA-DAF, was constructed. This vector codes for the production of a fusion protein of t-PA coupled to the last 37 amino acids of decay acceleration factor (DAF) (Caras, I. W., et al., *Science* 238:1280-1283 (1987)). The resulting DNA fragment encoding the t-PA-DAF fusion protein was then cloned into the polylinker region of pRK.CXHRN (Leung, D. W., et al., *Science*, 246:1306-1309 (1989)) in such a way that the expression of the fusion protein is directed by the CMV promoter. This plasmid, pRK-t-PA-DAF, was used as the starting material for all mutagenesis experiments.

The chimeric protein is targeted and displayed on the cell surface by a glycophospholipid membrane anchor. The general scheme for mutagenizing a defined region in the plasmid pRK-t-PA-DAF and for the screening of t-PA mutants is shown in FIG. 1. A 330 base pair (bp) cassette encoding amino acids 88-198 of the K1 region of t-PA and 10 amino acids of the K2 domain (Higgins, D. L. & Bennett, W. F. *Annu. Rev. Pharmacol. Toxil.*, 30:91-121 [1990]) was randomly mutagenized using PCR conditions of reduced Taq polymerase fidelity (Leung, D. W., Chen, E. Y. & Goeddel, D. V. *Technique*, 1:11-15 [1989]). Specifically, site directed mutagenesis (Kunkel, T. A., et al., *Methods in Enzymol.* 154:367-382 (1987)) was used to engineer two new restriction sites (Cla I at amino acids 86-87 and Nhe I at amino acids 199-200) into the coding region of t-PA without changing t-PA's amino acid coding sequence. PCR primers were then used to amplify the DNA region spanning the Cla I and Nhe I site using conditions of reduced Taq polymerase fidelity. The resulting mutagenized PCR products were digested with Cla I and Nhe I, and religated into the appropriate position of the t-PA DNA. The t-PA DNA had previously been digested with the same enzymes to remove the corresponding wildtype sequence.

A library of approximately $10^5$ independent clones was generated. The TSA-201 cell line, (related to human embryonic kidney cell line 293) was used for transfection at a transfection efficiency under these conditions of approximately 10%, which increased the percentage of single copy transfers (Rice, G. C., et al., *Cytometry* 12:221-233 [1991]). 48 hrs later the cells were removed from plates with 0.04% EDTA and stained with Mab387, directed to an epitope within the mutagenized K1 domain, and Mab372, directed to the nonmutagenized protease domain of t-PA. Cells were sorted for the absence of binding to Mab387 and positive staining for Mab372.

Typical bivariant FACS distributions obtained from transfected TSA201 cells are shown in FIG. 2. Briefly, mouse Mabs were either biotinylated or directly coupled with the fluorescein (FITC) or phycoerythrin (PE) as previously described (Woronicz, J., et al., *J. Immonol. Meth.* 120:291-296 [1989]). Streptavidin-FITC or streptavidin-PE were used to detect binding of biotinylated Mabs. Monoclonal antibody 387 is specific for the K1 domain of t-PA, while Mab372 is specific for the protease domain. These two Mabs were isolated and characterized using either K1 or protease domain deletion mutants of t-PA (Botstein, D. & Shortle, D. *Science* 229:1193-1201 [1985]). The samples were analyzed on a Coulter Elite or 753 flow sorter using 488 nM argon ion laser excitation with emission detected using a 525 nM (+/−25 nM) band pass filter for FITC and 575 nM(+/−25) for PE after electronically removing the PI staining cells (680 nM long pass filter) as described (Rice, supra). From the histogram of the unsorted cells, it is clear that most of the mutations did not disrupt the Mab387 epitope, as the expression profile of t-PA on the cell surface is similar to that with non-mutagenized pRK-t-PA-DAF. Plasmid DNA was recovered from cells derived from the top left quadrant, amplified and retransfected. A clearly defined shoulder of Mab387 epitope loss mutants was observed in the second sort. Plasmid DNA was recovered from cells sorted from this region and subsequent transfections were made using DNA derived from individual clones. Over 60% of the isolated clones were found to be epitope loss mutants after two rounds of sorting.

EXAMPLE II

Sequence and Epitope Analysis

Plasmid DNA's isolated from selected mutants were sequenced (Chen, E. Y. & Seeburg, P. H., *DNA* 4:165-170 [1985]) with a synthetic primer that hybridized to the coding strand of t-PA corresponding to amino acids 213-218.

DNA sequence comparison of the various K1 epitope loss mutants (Table 1) showed that four clones possessed single point mutations (clones k5, k10, 19 and 20), five clones possessed two amino acid substitutions (k3, 8, 11, 17, and 22), three clones with three substitutions, (k1, 2 and 9), one each with four (k7), five (k18), and 10 point mutations (k12). None of the mutants sequenced contained deletion or insertion mutations. The distribution of the point mutations appears not to be localized to any particular region of the K1 domain based on the predicted three dimensional (3-D) structure of K1 of t-PA ([Tulinsky, A., Park, C. H., Mao, B. & Llinas, M.*Proteins: Structure, Function and Genetics* 3:85-96

(1988)]; see FIG. 3). However, as Cys conversions are expected to disrupt the disulfide bridges, the loss of the Mab387 epitope in clones k1, k2, k5, k9, k12 and k18 may be due to changes in overall folding of K1. As clones k10 (V157D), k19 (N142S), and k20 (Y156D) contain single amino acid changes, the mutations found in these clones must be involved in loss of binding of Mab387. N142 is a residue found on the surface of the K1 structure and therefore is likely to be involved directly in Mab387 binding. Y156 and V157 are expected to be found in internal positions of K1 near the vicinity of N142, hence the loss of Mab387 binding in clones k10 and k20 are likely to be due to some local denaturation of the epitope as opposed to specific interaction with Mab387. The 3-D structure also predicts that W154 and N146 are located in internal positions of K1 that are distant from N142, clones k17, k22 and k8 with non-conservative changes in these residues are expected to have grossly disrupted K1 structures. The residues K159 in k11 and N115 in k3 are likely to be involved in Mab387 binding, as they are found in external positions in close proximity to N142. None of the four mutated residues found in k7 are in the vicinity of N142; however, G137 and D148 are conserved residues among the various Kringle structures (Tulinsky, et al., supra). Having mutations in these two residues may alter the conformation of K1.

TABLE 1

| Clone Number | Substitutions Found | HepG2 Binding | Clot Lysis |
|---|---|---|---|
| k01 | Y93C, T103A, N184S, G198D. | (−) | (+) |
| k02 | D150V, C168R, Y188C. | (+) | (+) |
| k03 | N115S, G139R. | (−) | (+) |
| k05 | C168S. | ND | ND |
| k07 | k124E, G137S, D148G, S165T. | (+) | (+) |
| k08 | N146I, G198D. | (−) | (+) |
| k09 | S127C, Y143H, C173R. | (−) | (+) |
| k10 | V157D. | (−) | (+) |
| k11 | R130Q, K159R. | (±) | (+) |
| k12 | R89G, W116R, k124E, D148G, Y156F, Y163C, N177S, Y181C, F182L, N184T. | (±) | (−) |
| k17 | G137D, W154R. | (−) | (+) |
| k18 | Q123R, C155R, S169T, N177T, T195A. | ND | ND |
| k19 | N142S. | (−) | (+) |
| k20 | Y156D. | (−) | (+) |
| k22 | N146D, L194P. | (−) | (−) |

A collection of 15 K1 mutants that lost the epitope for Mab387. The mutants are described by a wild-type residue/mutant residue convention; for instance, N142S means that asparagine at position 142 of t-PA has been substituted with serine.

While the invention has necessarily been described in conjunction with preferred embodiments, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by Letters Patent hereon be limited only by the appended claims and equivalents thereof.

All references cited herein are hereby expressly incorporated by reference.

What is claimed is:

1. A method for making a variant secretory protein retaining at least one desired binding property and eliminating at least one undesired binding property of the wild-type secretory protein comprising:
   (a) mutating the DNA encoding the selected wild-type protein thereby creating a library of related variant DNA molecules;
   (b) inserting each DNA molecule created in step (a) into an expression vector, wherein the vector comprises DNA encoding a transmembrane anchor domain thereby creating a library of vectors;
   (c) transfecting eukaryotic cells with the vectors of step (b);
   (d) culturing the cells of step (c) under conditions inducing the expression of the DNA to produce a chimeric fusion protein immobilized on the cell membrane;
   (e) contacting the cultured cells of step (d) with first and second reporter molecules capable of binding to different epitopes on the wild-type protein, each reporter molecule containing a fluorophore different from the fluorophore of the other reporter molecule, with said contacting taking place under conditions for which at least a portion of the cultured cells bind to the first or second reporter molecules;
   (f) sorting the contacted cells based on a desired binding pattern with the first or second reporter molecules; and
   (g) obtaining the variant proteins having the desired binding pattern from the sorted cells from (f).

2. The method of claim 1 wherein step (g) comprises isolating the variant protein from the sorted cells.

3. The method of claim 1 wherein step (g) comprises isolating the variant DNA molecule and producing the variant protein from the isolated variant DNA molecule by recombinant methods.

4. The method of claim 1 wherein step (g) comprises sequencing the variant DNA molecule, determining the codons encoding amino acids in the variant protein that produce the desired binding pattern, altering those codons in a DNA molecule encoding the wild-type protein, and producing the variant protein from the DNA containing the altered codons by recombinant methods.

5. The method of claim 1 wherein the first and second reporter molecules comprise a detectable marker conjugated to a molecule selected from the group; antibodies, ligands, and soluble receptors.

6. The method of claim 5 wherein the first and second reporter molecules comprise a first and a second monoclonal antibody (Mab) each conjugated to a different fluorophore.

7. The method of claim 6 wherein the sorting step comprises fluoresence activated cell sorting (FACS).

8. The method of claim 1 wherein the DNA encoding the transmembrane anchor domain encodes the membrane glycophospholipid anchor sequence of decay acceleration factor (DAF).

9. The method of claim 8 wherein the selected wild-type protein is selected from the group; growth hormone, human growth hormone (hGH), des-N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormone (FSH), thyroid stimulating hormone (TSH), leutinizing hormone (LH), glycoprotein hormone receptors, calcitonin, glucagon, factor VIII, an antibody, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, β-lactamase, tissue factor protein, inhibin, activin, vascular endothelial growth factor, integrin receptors, thrombopoietin, protein A or D, rheumatoid factors, NGF-β, platelet-growth factor, transforming growth factor; TGF-alpha and TGF-beta, insulin-like growth factor-I and -II, insulin-like growth factor binding proteins, CD-4, DNase, latency associated peptide, erythropoietin, osteoinductive factors, interferon alpha, -beta, and -gamma, colony stimulating factors (CSFs), M-CSF, GM-CSF, and G-CSF, interleukins (ILs), IL-1, IL-2, IL-3, IL-4, IL-6, IL-7, superoxide dismutase; viral antigens, HIV envelope proteins GP120 and GP140, immuno globulins, and fragments of the above-listed proteins.

10. The method of claim 9 wherein the protein is a human protein.

11. The method of claim 1 wherein the eukaryotic cell is a mammalian cell.

12. The method of claim 1 wherein the desired binding pattern comprises binding of the cells with the first reporter molecule and the absence of binding of the cells with the second reporter molecule.

* * * * *